United States Patent [19]
Cheskin et al.

[11] Patent Number: 5,807,574
[45] Date of Patent: Sep. 15, 1998

[54] HOMOGENEOUS MIXTURES OF LOW TEMPERATURE-MELTING DRUGS AND ADDITIVES FOR CONTROLLED RELEASE

[75] Inventors: Howard Cheskin, Glencoe; Thomas J. Hale, Chicago; Kurt G. Van Scoik; Ji Zhou, both of Grayslake, all of Ill.

[73] Assignee: Abbott Laboratories, Abbott Park, Ill.

[21] Appl. No.: 879,468

[22] Filed: Jun. 20, 1997

Related U.S. Application Data

[63] Continuation of Ser. No. 415,401, Apr. 3, 1995, abandoned.
[51] Int. Cl.⁶ .............................. A61K 9/48; A61K 9/52
[52] U.S. Cl. ..................... 424/451; 424/455; 424/457; 424/453; 424/452
[58] Field of Search ................... 424/451, 452, 424/465, 455, 457, 489, 468, 453, 454, 456

[56] References Cited

U.S. PATENT DOCUMENTS

| | | | |
|---|---|---|---|
| 2,887,438 | 5/1959 | Cooper et al. | 167/82 |
| 3,279,998 | 10/1966 | Raff et al. | 167/82 |
| 4,483,847 | 11/1984 | Augart | 424/22 |
| 4,885,175 | 12/1989 | Zibell | 426/5 |
| 4,913,906 | 4/1990 | Friedman et al. | 424/499 |
| 5,017,613 | 5/1991 | Aubert et al. | 514/557 |
| 5,019,398 | 5/1991 | Daste | 424/480 |
| 5,164,193 | 11/1992 | Okada et al. | 424/468 |
| 5,240,712 | 8/1993 | Smith et al. | 424/451 |
| 5,455,045 | 10/1995 | Samuels et al. | 424/451 |

FOREIGN PATENT DOCUMENTS

| | | |
|---|---|---|
| 0299668 | 1/1989 | European Pat. Off. . |
| 2549371 | 1/1985 | France . |
| WO 92/01446 | 2/1992 | WIPO . |
| WO 92/02145 | 2/1992 | WIPO . |

OTHER PUBLICATIONS

Bialer, M., et al., "Effect of sustained release on the pharmacokinetics of valproic acid in the dog", *IJP*, 20:53–63 (1984).

Bialer, M., et al., "Pharmacokinetic Evaluation of Novel Sustained–Release Dosage Forms of Valproic Acid in Humans", *Biopharmaceutics & Drug Disposition*, 6:401–411 (1985).

Bialer, M., et al., "Releation Between Absorption Half–Life Values of Four Novel Sustained–Release Dosage Forms of Valproic Acid in Dogs and Humans", *Biopharmaceutics & Drug Disposition*, 7:495–500 (1986).

Primary Examiner—Thurman K. Page
Assistant Examiner—James M. Spear
Attorney, Agent, or Firm—Michael J. Ward

[57] ABSTRACT

The present invention relates to novel compositions of and methods of manufacture of controlled release formulations obtained by mixing molten drugs with molten additives to produce homogeneous drug-additive composites.

4 Claims, 3 Drawing Sheets

HOMOGENEOUS MIXTURES OF LOW TEMPERATURE-MELTING DRUGS AND ADDITIVES FOR CONTROLLED RELEASE

This application is a continuation of U.S. patent application Ser. No. 08/415,401, filed Apr. 3, 1995, now abandoned.

FIELD OF THE INVENTION

The present invention provides novel compositions and methods of manufacturing controlled-release therapeutics comprising drugs which melt at low temperatures and an additive, such that the homogeneous composite contains 92–97% drug weight/weight (w/w).

BACKGROUND OF THE PRESENT INVENTION

Some medical conditions are best treated by administration of a pharmaceutical which is formulated to allow the active substance or ingredient to act as quickly as possible. Such a formulation may comprise an injectable solution or a readily-dissolvable tablet or capsule. This type of formulation is useful, for instance, for treating acute pain, such as headaches, or pain associated with sudden trauma resulting from an accident.

Other medical conditions are best treated by administration of a pharmaceutical in such a way as to sustain its action over an extended period of time. This type of administration is useful, for example, for treating chronic pain, such as that associated with rheumatic or arthritic conditions, or for the treatment of a chronic cardiovascular condition. It can be achieved by repeated administration of an immediate-release tablet or capsule at frequent intervals, for instance, every four to six hours. However, this is generally inconvenient, especially during the night, when it is often necessary to awaken a patient to administer the tablet or capsule. In addition, such multiple dosing may lead to undesirable fluctuations in the plasma concentration of the active substance.

It has previously been proposed to produce a formulation which will release the active substance therein at a controlled rate, such that the amount available in the body to treat the condition is maintained at a relatively constant level over an extended period of time. Particularly suitable periods are twelve hours and twenty-four hours, since such formulations need only be taken once or twice a day to maintain an effective treatment of the condition. Such formulations are generally known as "controlled-release formulations."

Many controlled-release formulations are already known, but there is no generally-applicable method by which such formulations can be designed. Each formulation is dependent on the particular active substance incorporated therein.

In designing a formulation, it is generally necessary to take into account many factors, including the rates of absorption and clearance of the active substance by the patient, the interaction of the active substance with the excipients and/or coatings to be used in the formulation, the solubility of the active substance and of the excipients and/or coatings, and the effects on the bioavailability of the active substance which may be caused by the excipients and/or coatings. It is, however, not readily possible to predict whether any particular formulation will provide the desired controlled-release, and it is generally found necessary to carry out substantial experimentation to produce a controlled-release formulation having the desired properties.

Over the years, considerable effort has been directed toward the preparation of such controlled-release formulations in the pharmaceutical industry. Specifically, controlled-release compositions have been sought to deliver a controlled drug release over a long time without fragmentation of the composition in vivo.

WO 92/02145 to Warner-Lambert Corporation teaches a flavor delivery system by combining a flavor, resin and a polyalkylene wax in a liquid mixture. The resin and the wax protect, hold and mask the aroma of the flavor component. It is unclear what effect of mixing the wax with the resin has on the retention of the aroma of the flavor component.

U.S. Pat. No. 4,885,175 to Zibell teaches a chewing gum with delayed release which comprises macroscopic flavorer or sweetener mixed with a molten wax to produce a damp mix. The wax comprises 10–50% weight of the damp mix.

WO 92/01446 to APS Research Limited discloses application of a subcoat of a drug migration controlling agent (DMCA) to drug granules. The DMCA is a wax or wax-like material and is typically a long chain alcohol, acid or ester, paraffin wax, or a silicone wax. The DMCA is applied as a surface treatment on macroscopic drug granules.

U.S. Pat. No. 4,483,847 to Augart teaches using a high-melting and a low-melting lipid or lipoid material to produce a retarded liberation of active material. The solid active material and the high-melting lipid are embedded in the low-melting lipid at a temperature sufficient to melt the low-melting lipid but not the high-melting lipid. The mixture after cooling is ground to give a granulate which is then pressed into a tablet.

Pharmaceutical compositions comprising low-melting drugs are one such example wherein controlled-release formulations are already known, but there is no generally-applicable method by which such formulations can be designed.

In U.S. Pat. No. 5,017,613 to Aubert et al., liquid valproic acid (VPA) and solid ethyl cellulose are added slowly to a powdered sodium valproate to form a granular agglomeration. Precipitated silica is added to the granulate and compressed to tablets. The tablets are then lacquered.

The use of additives, particularly waxes, with low-melting drugs has had limited success in producing controlled-release formulations. An example of a low-melting drug is sodium hydrogen divalproex, an active ingredient in anti-epileptic drugs.

In formulations, VPA is a liquid at room temperature, thereby making it difficult to formulate a tablet. One way to tablet a form of VPA is to mix VPA with an equimolar amount of sodium to form sodium valproate. However, sodium valproate is difficult to work with due to its hygroscopic characteristics.

U.S. Pat. No. 4,913,906 to Friedman et aL, discloses controlled-release formulations of VPA combined with an additive, such as carboxymethylcellulose, ethylcellulose or waxes, such as paraffin. The additives are added as solids and are used to granulate the VPA which is then pressed to a tablet. The active ingredient comprises 10–80% weight of the dosage form. The additives are formulated with VPA as solids.

What the prior art fails to teach is formulations of therapeutics where a liquid active ingredient is combined with a liquid additive to provide a homogeneous mixture which provides controlled-release of the active substance. The present invention relates to drug/additive compositions which give controlled-release of drug over a long time period after oral dosing.

SUMMARY OF THE INVENTION

Figure 1:
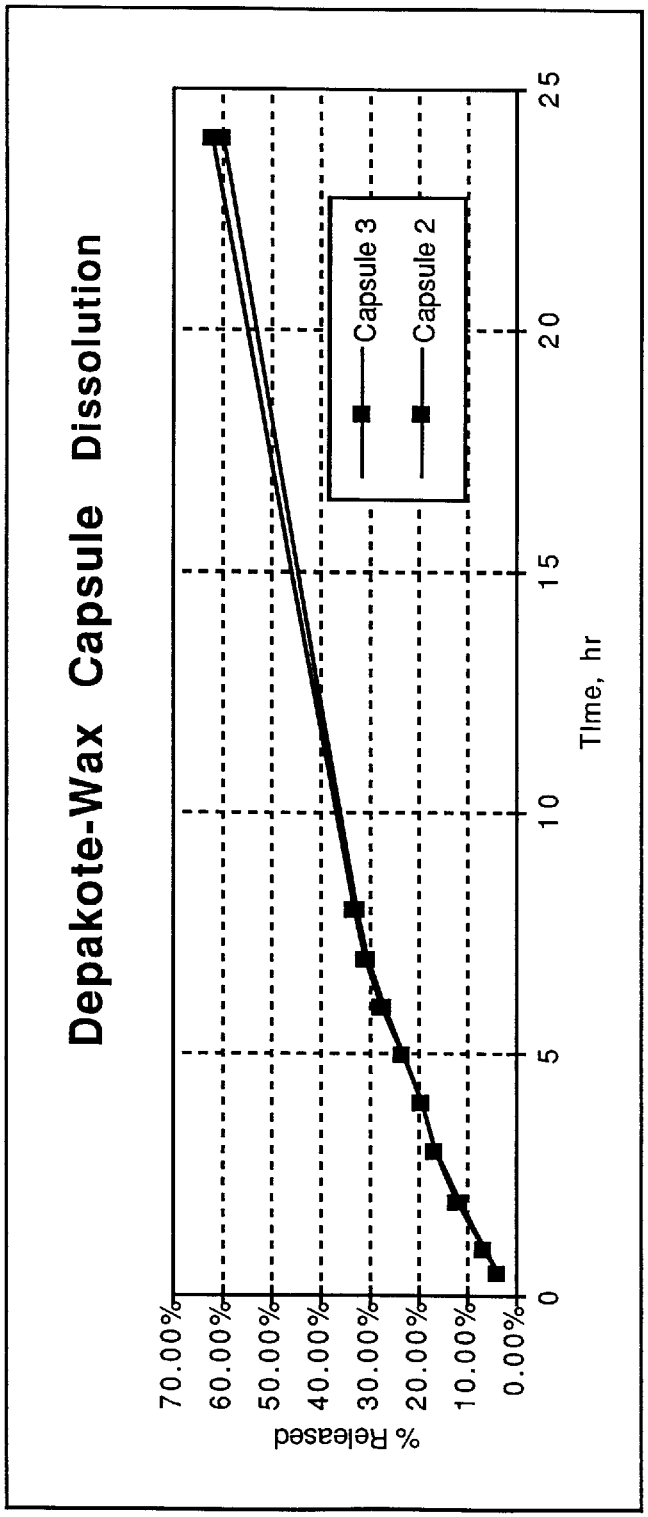
FIG. 1 depicts the results from a dissolution study. A sodium hydrogen divalproex and polyethylene wax mixture comprise a controlled-release capsule. Sodium hydrogen divalproex comprises 95.2% w/w of the drug-additive composite.

The present invention relates to compositions of controlled-release therapeutics. The controlled-release therapeutics of the present invention comprise low temperature-melting drugs that are melted and mixed with a molten additive to give a homogeneous, liquid mixture. The drug comprises 92–97% w/w of the drug-additive composite.

The present invention also relates to methods of manufacturing controlled-release therapeutics comprising melting low temperature-melting drugs and an additive by mixing the drug and additive to provide a homogeneous drug-additive mixture, and allowing them to harden to form a drug-wax composite.

DETAILED DESCRIPTION OF THE PRESENT INVENTION

The present invention is directed to compositions of and methods of manufacturing controlled-release orally administered drugs. The compositions are in a drug-additive composite, which show sustained release of the drug over time.

One embodiment of the present invention includes melting a low temperature-melting drug (a drug which melts below 150° Centigrade (C.)) and combining it in a liquid state with a molten additive. More preferably, the low temperature-melting drugs melt at 125° C. or below. Examples of drugs which melt at low temperatures include, but are not intended to be limited to, sodium hydrogen divalproex, ibuprofen, ramipril, dibenzyline, erythrityl tetranitrate, isosorbide dinitrate, methosuximide, ketoprofen, gemfibrozil, paroxetine hydrochloride, and trimipramine maleate. Sodium hydrogen divalproex has a melting point of approximately 100 ° C. while ibuprofen has a melting point between 75° and 77° C.

The additives may be melted with the low temperature-melting drugs or they may be melted separately and later combined in liquid form with the molten drug. If the additive is melted with the low temperature-melting drug, the additive must have a melting point at or below the melting point of the drug. If the melting point temperature of the additive is higher than the melting point temperature of the drug, the melting point of the additive must be such that the higher temperature would not cause drug degradation. Similarly, if the additive is melted separately from the drug it must be at a temperature such that when combined with the molten drug, it does not cause drug degradation.

Additives that are acceptable for use with the present invention include derivatives of cellulose, such as ethyl cellulose, methylcellulose, hydroxypropyl cellulose, polyacrylamide, ethylene vinyl acetate copolymer, polymethylmethacrylate, polyhydroxyethyl methacrylate and waxes. Preferably, the waxes are polyalkylene waxes, which can be natural or synthetic, such as polyethylene wax. Polyethylene wax has a melting point of approximately 97.8° C. and when molten, forms a homogeneous mixture with the molten drug without adversely affecting the drug. Polyethylene wax will also remain a solid in vivo thereby providing a matrix through which drug can diffuse. It is to be understood by those skilled in the art that the additives used in the drug-additive composite must be pharmaceutically acceptable for its intended use.

The additives must also not adversely affect the ability of the low-melting drug and the additive to form a homogeneous drug-additive composite. The homogenous drug-additive composite provides for a more intimate mixture of drug and additive molecules, as opposed to simply dispersing solid drug particles in a liquid additive. For purposes of the present invention, the term "composite" refers to the homogeneous drug-additive mixture after it has solidified and is not meant to include the capsule which in some embodiments of the present invention contains the composite. Generally, the molten, homogeneous mixture may be added to a capsule wherein it cools and hardens. Cooling times can be from a few seconds minutes. However, the cooling time is fast enough so that a homogeneous drug-additive composite is produced. Other vehicles, which provide the same functions of the capsule, such as containment of and a site for cooling of the molten, homogeneous mixture, can be used as well. In addition, the molten, homogeneous mixture may be poured into molds where upon hardening the drug-additive composite may be removed from the mold and further processed or used.

The homogeneous drug with additive composite allows for controlled-release over time. The additive in the drug-additive composite provides a matrix structure, due to its ability to remain a solid in vivo, which allows drug to diffuse through the matrix over time.

Different types of capsules may be utilized with the formulations of the present invention. For example, Capill™ capsules are an injection-molded, starch-based hard shell which may be filled and sealed manually or by using specialized manufacturing equipment. Another example of a capsule that may be used with the formulations of the present invention are Vegicap™, a hydroxypropylmethylcellulose hard shell that is similar in size and shape with standard gelatin capsules and may be filled using standard capsule-filling equipment. In addition, soft or hard shell capsules may be used provided that the molten, homogenous mixture does not melt the capsule. The compositior of a soft elastic gelatin capsule typically comprises from about 30% to about 50% by weight of gelatin, from about 20% to about 30% by weight of a plasticizer, and from about 25% to about 40% by weight of water.

Various methods may be used for manufacturing and filling the capsules. For example, seamless capsule methods, rotary methods, methods using a Liner machine or an Accogel machine, and the like, may be used. Also various manufacturing machines may be used for manufacturing the capsules. The target filling volume/weight depends on the potency of the molten filling solution in combination with the desired dosage strength.

It is to be understood by those skilled in the art that a particular capsule is not a critical part of the present invention but is a vehicle for delivering a homogeneous drug-additive composite. However, if a capsule is used to deliver the drug-additive composite, it is necessary that the capsule maintain its structural integrity while the molten drug-additive mixture hardens. It is also necessary that the capsule dissolves after it is administered in vivo thereby facilitating drug release from the drug-additive composite.

Several advantages result from the present invention. First, complicated coatings of the drug-additive composite are not needed for a controlled-release of drug. Molten, homogeneous drug-additive mixture can be added to a capsule and allowed to harden by cooling. The capsule containing the drug-additive composite may then be capped.

Another advantage is there is no need for expensive tabletting equipment because the molten, homogeneous drug-additive mixtures may be added directly to a preformed capsule.

Yet another advantage of the present invention is that the drug-additive composite allows slow, regular diffusion of drug out of the drug-additive composite due to the solid matrix from which diffusion of drug can occur over time.

Still yet another advantage of the present invention is that since both the drug and additive are mixed as liquids to form a homogenous mixture, the drug and additive molecules are in a more intimate, uniform contact with each other, as opposed to where relatively large macroscopic drug particles are merely dispersed in a liquid additive. Macroscopic drug particles are relatively large particles which have their surfaces coated with liquid additive. The more intimate nature of the molten, homogeneous drug-additive mixture ensures a more uniform matrix upon cooling from which diffusion of drug can occur.

Still yet another advantage of the present invention is that the present invention allows for high drug loading with the additive. Drug loading of the drug-additive composite can comprise 92–97% drug (w/w).

Once the molten drug and molten additive are mixed it is added to a capsule, mold, or other suitable vehicle. The homogeneous mixture can be added by pipet, poured or added by more sophisticated instrumentation. Once the homogeneous mixture has hardened, it can be capped and sealed as the final product. Capping and sealing the final product may include using solvents such as ethanol.

The additive used in the method of the present invention are generally polyalkylene waxes. Preferably, polyethylene wax is used in the drug-wax composite.

The following Examples are used to illustrate the scope of the present invention and is not intended to be limited to the Examples themselves.

Example 1

A dissolution test was carried out to determine the quantity of sodium hydrogen divalproex which went into solution in an artificial medium with a phosphate buffer at pH 7.5. The quantity of VPA was determined by measuring VPA concentrations in samples taken from the dissolution medium.

A 25 gram (gm) sample of sodium hydrogen divalproex (Abbott Laboratories, Abbott Park, Ill. 60064) containing sodium hydrogen divalproex was melted in a beaker on a hot plate with 1.25 gm of polyethylene wax (S-390 C, Shamrock Technologies Inc., Newark, N.J. 07114) at approximately 115° C. The resulting sodium hydrogen divalproex-wax melt was mixed to form a sodium hydrogen divalproex-wax composite. Size 00 Capill™ capsules (Capsugel Corp., Greenwood, S.C. 29646), were filled with the molten sodium hydrogen divalproex-wax mixture by transferring the molten mixture using glass Pasteur pipets. The tip end of the pipets were shortened to increase the flow of the molten mixture. The molten mixture was allowed to solidify by cooling for approximately 30 seconds. The Capill™ capsules were then capped and sealed with a 20% ethanol in water solution. Individual capsules were tested in USP Dissolution Apparatus II with a rotating paddle (VanKel Industries, Edison, N.J. 08820) for four hours in simulated gastric fluid without pepsin and then in simulated intestinal fluid without pancreatin, pH of 7.5. The gastric fluid without pepsin was made by dissolving 2.0 gm of sodium chloride (Sigma Chemical Co., St. Louis, Mo. 63178) in 7.0 milliliters (ml) of hydrochloric acid (Sigma) and adding water to 1000 ml. The simulated intestinal fluid without pancreatin was made by dissolving 6.8 gm of monobasic potassium phosphate in 250 ml of water and mixed. Added to the solution was 190 ml of 0.2 N sodium hydroxide to a pH of 7.5. The solution was diluted with water to 1000 ml.

Samples (2 ml) were removed at predetermined times and concentrations of VPA measured on the TDx® Analyzer (Abbott Laboratories, Abbott Park, Ill. 60064). Results are shown in Table 1. Percentages in Table 1 reflect the percent sodium hydrogen divalproex released from the composite based on VPA measurements. FIG. 1 is a graphic representation of the data showing controlled-release over 24 hours.

The capsules showed controlled release of sodium hydrogen divalproex such that only approximately 60% of the sodium hydrogen divalproex in the sodium hydrogen divalproex-wax composite was released over 24 hours.

TABLE 1

| Time (hours) | Capsule 2 | Capsule 3 |
| --- | --- | --- |
| 0.5 | 3.80% | 4.00% |
| 1 | 6.70% | 6.90% |
| 2 | 11.50% | 12.30% |
| 3 | 17.00% | 16.50% |
| 4 | 19.60% | 19.30% |
| 5 | 23.60% | 23.50% |
| 6 | 27.60% | 27.40% |
| 7 | 31.00% | 30.50% |
| 8 | 33.60% | 33.00% |
| 24 | 62.60% | 60.10% |

Example 2

A dissolution test was done as in Example 1. 25 gm samples of sodium hydrogen divalproex (Abbott Laboratories), which were combined with 0.875 gm and 1.75 gm polyethylene wax (S-390 C, Shamrock Technologies Inc.). The sodium hydrogen divalproex and polyethylene wax were melted in a beaker on a hot plate at a temperature of approximately 115° C. The resultant sodium hydrogen divalproex-wax melt was mixed to form a homogeneous sodium hydrogen divalproex-wax mixture. The molten sodium hydrogen divalproex-wax composite was filled into Capill™ capsules. The molten mixture was transferred to the Capill™ capsules using glass Pasteur pipets which had been shortened at the tip end to increase flow of the molten mixture. The Capill™ capsules were then capped and sealed with a 20% ethanol in water solution.

Figure 2:
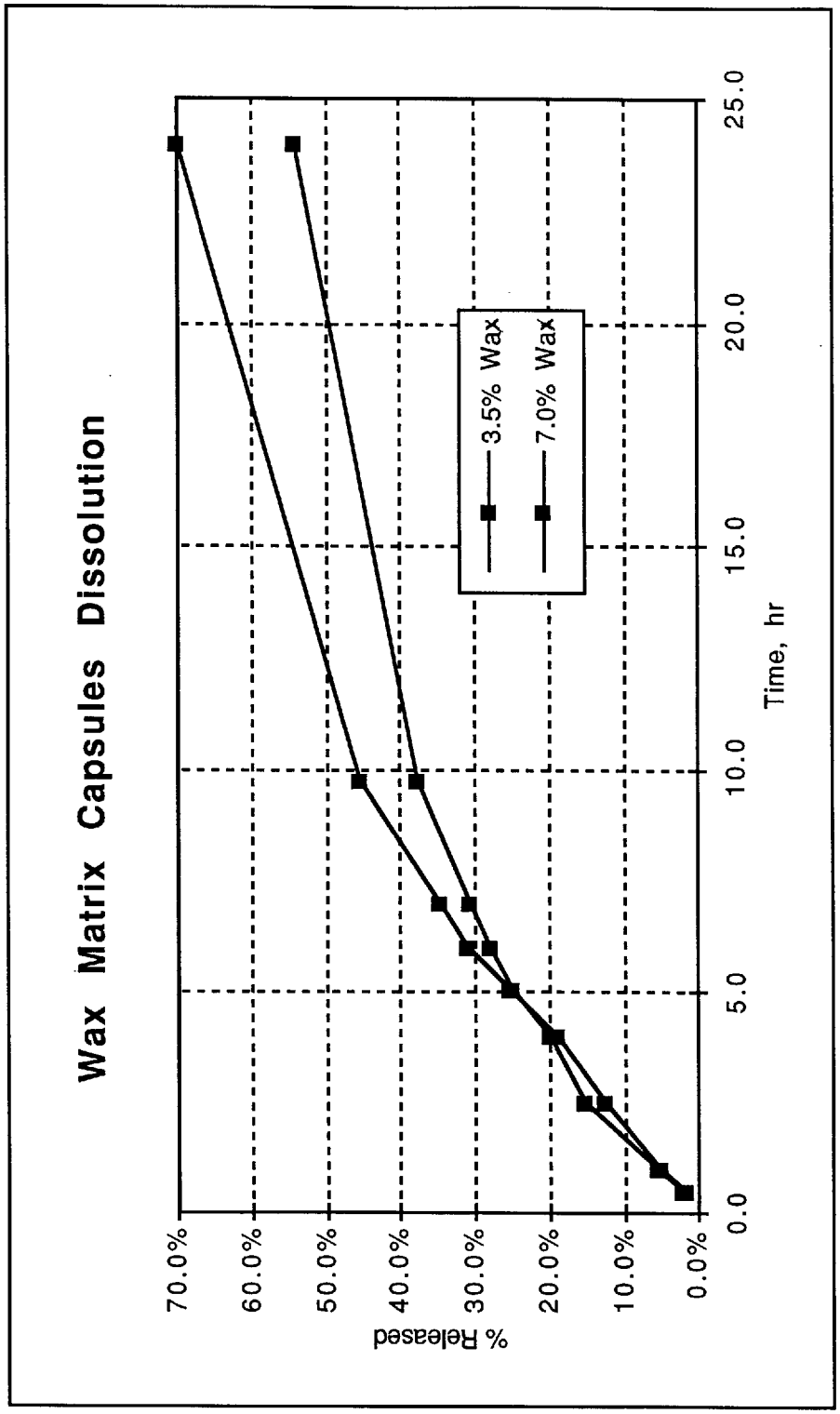
FIG. 2 depicts the results from a dissolution study with 93% w/w drug loaded composite capsules and 96.5% w/w drug loaded composite capsules.

The dissolution liquids were prepared as described in Example 1 and the procedure of Example 1 was followed. Samples (2 ml) were removed at predetermined times (0.5, 1, 2, 4, 5.1, 6, 7, 9.8, and 24 hours) and concentrations of VPA measured on the TDx® Analyzer (Abbott Laboratories, Abbott Park, Ill. 60064). Results are shown in Table 2 and Table 3. Percentages in Table 2 and Table 3 reflect the percent sodium hydrogen divalproex released from the composite based on VPA measurements. FIG. 2 is a graphic representation of the data showing controlled-release over 24 hours.

The capsules showed controlled release of sodium hydrogen divalproex such that only 55% of the sodium hydrogen divalproex in the sodium hydrogen divalproex-wax composite was released in the 93% w/w drug loaded capsule over 24 hours while only 70% of the sodium hydrogen divalproex in the sodium hydrogen divalproex-wax composite was released in the 96.5% w/w drug loaded capsule for the same time period.

TABLE 2

96.5% Drug

| Time, hr | Capsule 1 % Release | Capsule 2 % Release | Capsule 3 % Release |
|---|---|---|---|
| 0.5 | .5% | 1.8% | 1.4% |
| 1.0 | .0% | 5.2% | 4.6% |
| 2.5 | 13.4% | 13.5% | 11.4% |
| 4.0 | 21.0% | 18.4% | 17.9% |
| 5.1 | 26.9% | 24.8% | 24.6% |
| 6.0 | 31.5% | 30.9% | 30.6% |
| 7.0 | 35.0% | 34.4% | 35.0% |
| 9.8 | 45.2% | 44.9% | 45.9% |
| 24.0 | 70.0% | 68.9% | 70.7% |

TABLE 3

93% Drug

| Time, hr | Capsule 1 % Release | Capsule 2 % Release | Capsule 3 % Release |
|---|---|---|---|
|  | 2.2% | 1.9% | 2.0% |
| 1.0 | 5.8% | 5.2% | 5.5% |
| 2.5 | 13.9% | 16.4% | 15.1% |
| 4.0 | 19.4% | 20.4% | 19.9% |
| 5.1 | 25.4% | 24.6% | 25.0% |
| 6.0 | 28.4% | 27.6% | 28.0% |
| 7.0 | 31.4% | 29.9% | 30.7% |
| 9.8 | 39.2% | 36.7% | 37.9% |
| 24.0 | 55.1% | 53.1% | 54.1% |

Example 3

Figure 3:
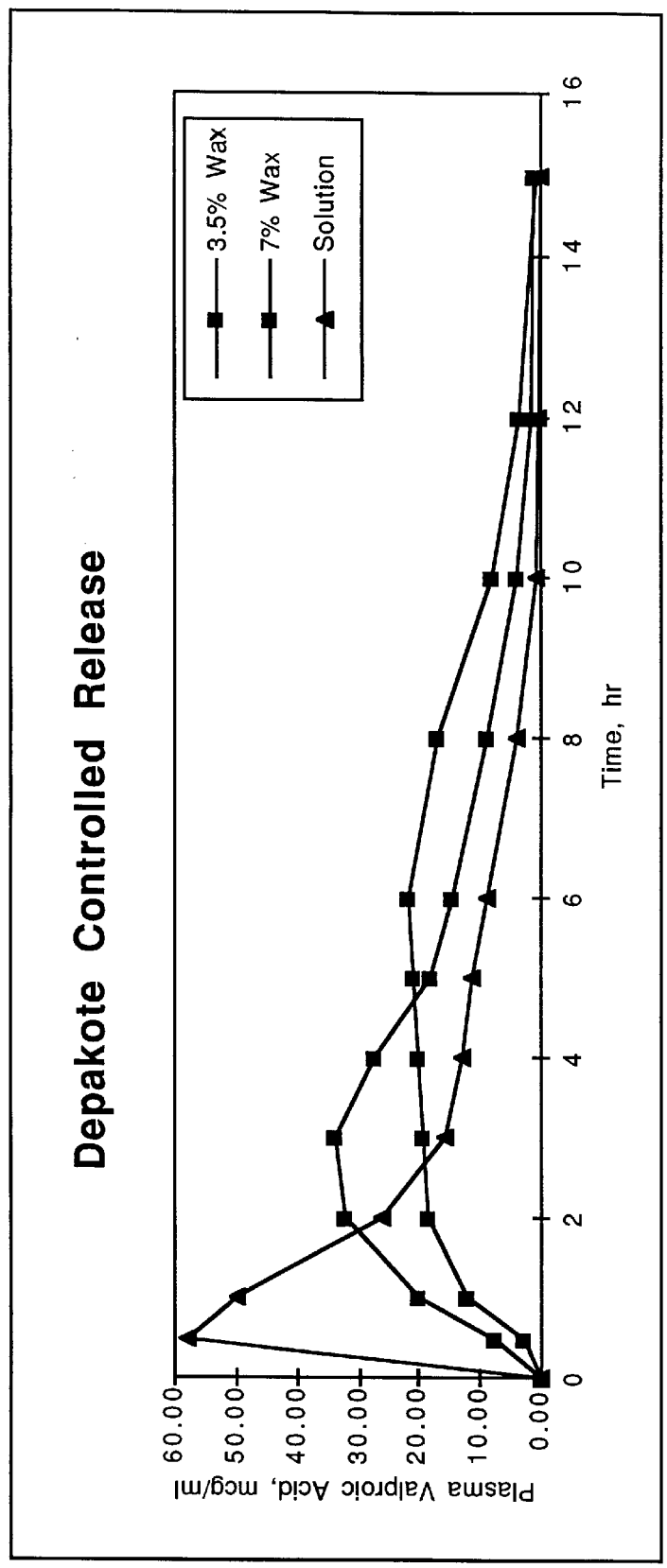
FIG. 3 depicts in vivo studies in dogs with three separate formulations including a sodium valproate solution, a drug-additive composite comprising 93% w/w drug, and a drug-wax composite comprising 96.5% w/w drug.

Nine beagle dogs were fasted overnight and fed prior to dosing. Each dog was tested with a capsule containing a 93% w/w sodium hydrogen divalproex-wax composite (approximately 515 milligrams (mg) of VPA equivalents), 96.5% w/w sodium hydrogen divalproex-wax composite (approximately 534 mg VPA equivalents), and a sodium valproate solution (approximately 500 mg of VPA equivalents). Each dog received each of the three formulations with a week between dosings for the drug to clear. Blood samples were drawn before dosing and at 30 minutes, 1, 2, 3, 4, 5, 6, 8, 10, 12, and 15 hours post dosing. EDTA was used as an anticoagulant in the blood tubes. The plasma was isolated and frozen prior to measurement. Plasma VPA concentrations were measured with the TDx® Analyzer (Abbott Laboratories, Abbott Park, Ill. 60064). The results are shown in FIG. 3. All determinations at each time point are the average of 9 measurements. As shown in FIG. 3, the sodium valproate solution peaks directly after administration and then shows a rapid decline of plasma VPA over time while the sodium hydrogen divalproex-wax composite formulations showed a delayed peak between 2–3 hours and consistently higher plasma VPA levels than the sodium valproate solution after 3 hours.

Capsules were made by taking 25 gm samples of sodium hydrogen divalproex (Abbott Laboratories) which were combined with 0.875 gm and 1.75 gm polyethylene wax (S-390 C, Shamrock Technologies Inc.). The sodium hydrogen divalproex and polyethylene wax were melted in a beaker on a hot plate at a temperature of approximately 115° C. The resultant sodium hydrogen divalproex-wax melt was mixed to form a homogeneous sodium hydrogen divalproex-wax mixture. The molten sodium hydrogen divalproex-wax composite was filled into Capill™ capsules. The molten mixture was transferred to the Capill™ capsules using glass Pasteur pipets which had been shortened at the tip end to decrease resistance to flow. After the homogeneous mixture had hardened, the Capill™ capsules were filled again with more of the homogeneous sodium hydrogen divalproex-wax mixture to a total of approximately 596 mg of sodium hydrogen divalproex-wax composite. The Capill™ capsules were then capped and sealed with a 20% ethanol in water solution.

We claim:

1. A controlled-release formulation comprising, in combination a therapeutically-effective dosage of drug which melts at low temperature and a polyethylene wax, such that the wax and drug form a homogeneous drug-additive composite with a 92–97 weight/weight of said drug.

2. The formulation of claim 1 where said drug is selected from the group consisting of sodium hydrogen divalproex, ibuprofen, ramipril, dibenzyline, erythrityl tetranitrate, isosorbide dinitrate, methosuximide, ketoprofen, gemfibrozil, paroxetine hydrochloride, and trimipramine maleate.

3. A method for manufacturing a controlled-release formulation comprising, in combination:

a) melting a drug an additive at a temperature below 150° Centigrade, mixing said drug and said additive to produce a homogeneous mixture, said drug comprising 92–97% w/w of said said homogeneous mixture;

b) adding said homogenous mixture to a capsule;

c) allowing said homogeneous mixture to harden to produce a drug-additive composite; and d) capping said capsule.

4. The method of claim 3 wherein said drug is selected from the group consisting of sodium hydrogen divalproex, ibuprofen, ramipril, dibenzyline, erythrityl tetranitrate, isosorbide dinitrate, methosuximide, ketoprofen, gemfibrozil, paroxetine hydrochloride, and trimipramine maleate.

* * * * *